US012655414B2

(12) United States Patent
Oharuda et al.

(10) Patent No.: US 12,655,414 B2
(45) Date of Patent: Jun. 16, 2026

(54) CELL OR TISSUE EMBEDDING DEVICE

(71) Applicants:Japan Vam & Poval Co., Ltd., Osaka (JP); National University Corporation Tohoku University, Sendai (JP)

(72) Inventors: Akinobu Oharuda, Osaka (JP); Yoshihiro Kimura, Osaka (JP); Masafumi Goto, Sendai (JP)

(73) Assignees: Japan Vam & Poval Co., Ltd., Osaka (JP); National University Corporation Tohoku University, Sendai (JP)

( * ) Notice: Subject to any disclaimer, the term of this patent is extended or adjusted under 35 U.S.C. 154(b) by 965 days.

(21) Appl. No.: 16/487,403

(22) PCT Filed: Feb. 23, 2018

(86) PCT No.: PCT/JP2018/006662
§ 371 (c)(1),
(2) Date: Aug. 20, 2019

(87) PCT Pub. No.: WO2018/155622
PCT Pub. Date: Aug. 30, 2018

(65) Prior Publication Data
US 2020/0231960 A1     Jul. 23, 2020

(30) Foreign Application Priority Data
Feb. 23, 2017    (JP) .............................. JP2017-032742

(51) Int. Cl.
| | |
|---|---|
| *C12N 11/04* | (2006.01) |
| *A61K 35/39* | (2015.01) |
| *A61K 47/32* | (2006.01) |
| *C12N 5/00* | (2006.01) |

(52) U.S. Cl.
CPC .............. *C12N 11/04* (2013.01); *A61K 35/39* (2013.01); *A61K 47/32* (2013.01); *C12N 5/0068* (2013.01); *C12N 2533/30* (2013.01)

(58) Field of Classification Search
CPC ................................................... A61K 35/28
See application file for complete search history.

(56) References Cited

U.S. PATENT DOCUMENTS

| | | | |
|---|---|---|---|
| 5,187,226 A | 2/1993 | Kamachi et al. | |
| 5,679,371 A | 10/1997 | Tanihara et al. | |
| 5,880,216 A | 3/1999 | Tanihara et al. | |
| 5,980,883 A | 11/1999 | Tanihara et al. | |
| 6,162,864 A | 12/2000 | Tanihara et al. | |
| 2004/0068039 A1 | 4/2004 | Lyoo et al. | |
| 2004/0133188 A1* | 7/2004 | Vardi ...................... A61F 2/022 424/93.1 |
| 2006/0246043 A1 | 11/2006 | Inoue et al. | |

FOREIGN PATENT DOCUMENTS

| | | |
|---|---|---|
| CN | 1376067 A | 10/2002 |
| JP | 08-116963 A | 5/1996 |
| JP | 10-043286 A | 2/1998 |
| JP | 10-072509 A | 3/1998 |
| JP | 11-092524 A | 4/1999 |
| JP | 2000-212288 A | 8/2000 |
| JP | 2003-102748 A | 4/2003 |
| JP | 2004-331643 A | 11/2004 |
| JP | 2004-334643 A | 11/2004 |
| WO | WO 98/04616 A1 | 2/1998 |

OTHER PUBLICATIONS

Matsuzawa et al., Die Makromolekulare Chemie, 1974, 175:31-41.*
Yamamoto et al., Polymer Journal, 1992, 24(1):115-119.*
Kim et al., Biomaterials, 2015, 40:51-60.*
De Carlo et al., International J of Molecular Medicine, 2010, 25:195-202.*
Masci et al., Macromol. Biosci, 2003, 3(9):455-461.*
Risbud et al., Cell Transplantation, 2000, 9:25-31.*
Burczak, Krystyna et al., "Long-term in vivo performance and biocompatibility of poly(vinyl alcohol) hydrogel macrocapsules for hybrid-type artificial pancreas" Biomaterials, 1996, pp. 2351-2356, vol. 17.
Inagaki, Akiko et al., "Evaluation of in-vitro immunoisolation function in immunoisolation device for cell transplantation, composed of hydrogel" Feb. 2017, p. 317, vol. 16, Extra Edition, O-36-6.
Sumi, Shoichiro et al., "Review: Macro-Encapsulation of Islets in Polyvinyl Alcohol Hydrogel" Journal of Medical and Biological Engineering, 2014, pp. 204-210, , vol. 34, No. 3.
International Search Report for PCT/JP2018/006662 dated May 29, 2018.
International Preliminary Report on Patentability for PCT/JP2018/006662 dated Sep. 6, 2019.
Supplementary European Search Report for EP 18757371 dated Dec. 2, 2020.
Nissin Chemical Industry Co., Ltd., "What are emulsions?", https://www.nissin-chem.co.jp/english/emulsion/, retrieved on Oct. 24, 2024.

* cited by examiner

*Primary Examiner* — Nghi V Nguyen
(74) *Attorney, Agent, or Firm* — Knobbe Martens Olson & Bear LLP

(57) ABSTRACT

A cell or tissue embedding device highly capable of supplying a physiologically active substance is disclosed. The device includes an aqueous gel that serves as an immunoisolation layer and the aqueous gel includes a polyvinyl alcohol resin with a syndiotacticity of 32 to 40% in triad. A process of preparing a PVA gel containing living cells or living tissue is disclosed and the process provides less reduction of the living cells or living tissue during preparation of the PVA gel.

13 Claims, 3 Drawing Sheets

Days after transplantation (day)

Days after transplantation (day)

Blood sugar level (mg/dL)

Days after transplantation (day)

Comparative Example 6

Comparative Example 7

Comparative Example 8

Comparative Example 10

Comparative Example 11

Pancreas

Pancreatic islets
for transplantation

Separation of
pancreatic islets

Pancreatic islets

Antibodies,
complements,
immune-related cells

Glucose, oxygen

Insulin

Mesh

Pancreatic islets

Effective building of
vascular network

Easy removal
and replacement

CELL OR TISSUE EMBEDDING DEVICE

CROSS REFERENCE TO RELATED APPLICATIONS

This application is a U.S. National Phase Application of PCT International Application Number PCT/JP2018/006662, filed on Feb. 23, 2018, designating the United States of America and published in the Japanese language, which is an International Application of and claims the benefit of priority to Japanese Patent Application No. 2017-032742, filed on Feb. 23, 2017. The disclosures of the above-referenced applications are hereby expressly incorporated by reference in their entireties.

TECHNICAL FIELD

The present invention relates to an aqueous gel for forming an immunoisolation layer of a cell or tissue embedding device which enables transplantation of a biological component that produces and/or secretes a physiologically active substance, such as a hormone or a protein, useful for a living organism, or of a biological component that has a detoxifying action on a harmful substance, and after the transplantation, exerts a preventive and/or therapeutic effect on diseases in animals including humans, such as an endocrine disease and a metabolic disease.

BACKGROUND ART

A cell or tissue embedding device is a device which contains living cells, living tissue, or the like and is used as a substitute for an organ etc. of a diseased human or animal for the purpose of preventing and/or treating a disease in a patient by supplying, to the patient, a hormone, a protein, or other physiologically active substances associated with metabolic function, or detoxifying a harmful substance. The cell or tissue embedding device is advantageous in that the living cells or living tissue can be protected by the immunoisolation layer from the biological defense mechanism and therefore the need for immunosuppressant administration and associated side effects can be avoided unlike living organ transplantation, that the operation is less invasive, and that the device enables, in addition to homologous artificial organ transplantation from a dead donor, transplantation of various regenerated stem cells and heterologous artificial organ transplantation, solving the problem of donor shortage.

In recent years, studies have been made on cell or tissue embedding devices comprising a material, such as a general polymer, a metal, or a ceramic, combined with living cells or living tissue or a cell preparation thereof, and such a device can be applied to the treatment of various diseases by changing the kind of the cells or the like contained therein.

For example, bioartificial pancreatic islets containing insulin-secreting cells (for example, pancreatic islet cells) are used to supply insulin as a hormone to a patient to thereby improve the blood sugar level.

In addition, bioartificial organs, such as a blood coagulation factor producing bio-artificial organ, a growth hormone producing bio-artificial organ, a parathyroid hormone producing bio-artificial organ, and a dopamine producing bio-artificial organ, are under examination for the therapy of diseases, such as hemophilia, hypophyseal dwarfism, hypoparathyroidism, and Parkinson's disease.

The cell or tissue embedding devices are supplied in various forms, and examples thereof include a device using a microcapsule or macrocapsule preparation in which living cells or living tissue is encapsulated in a polymer (for example, cell preparation). Such a device is characterized in that the strong cross-linked structure of the polymer protects the cells or tissue from the biological defense mechanism and that a hormone or the like secreted from the cells or tissue is supplied to a living organism using the molecular permeability of the polymer.

In recent years, polyvinyl alcohol (hereinafter may be abbreviated to PVA) has attracted attention as a polymer used for a bio-artificial organ etc. in which macrocapsule cell preparation is used.

PVA is a highly safe material which can be made into a gel by a chemical or physical treatment. PVA has a relatively high gel strength, and can be formed into various shapes. Examples of the chemical treatment used include a method in which glutaraldehyde (a crosslinking agent) and hydrochloric acid (a catalyst) are added to an aqueous solution containing PVA (see, for example, Non Patent Literature 1). Examples of the physical treatment used include a method in which an aqueous solution containing PVA is made into a gel by rapid cooling at a low temperature of about $-20°$ C. (Patent Literature 1).

CITATION LIST

Patent Literature

Patent literature 1: JP 10-43286 A
Patent literature 2: JP 2004-331643 A

Non Patent Literature

Non Patent Literature 1: Krystyna Burczak et al., Long-term in vivo performance and biocompatibility of PVA hydrogelmacrocapsules for hybrid-type artificial pancreas, Biomaterials, 1996, vol. 17, 2351-2356

SUMMARY OF INVENTION

Technical Problem

The gelation method using a chemical treatment as described above has a problem of cell damage caused by the crosslinking agent remaining in the PVA gel or by the low pH level after the addition of the catalyst, which reduces the number of living cells or the capability of supplying the physiologically active substance. As a result, the desired treatment effect cannot be obtained.

The gelation method using a physical treatment does not use any chemical agent and does not cause damage by a crosslinking agent or a catalyst, but the rapid cooling at the low temperature reduces the number of living cells or the capability of supplying the physiologically active substance.

As a method for solving these problems, disclosed is a method in which the preparation of the PVA gel at a low temperature is performed in the co-existence of a cell preservative with living cells (Patent literature 2). However, in this method also, a low temperature $(-80°$ C.) treatment for 24 hours is performed to prepare a PVA gel, and therefore, the problem of reducing the number of living cells or the capability of supplying the physiologically active substance cannot be sufficiently solved.

In light of the current situation described above, an object of the present invention is to provide a cell or tissue embedding device highly capable of supplying a physiologically active substance, by curbing the reduction of living cells or living tissue in the process of preparing a PVA gel containing the living cells or living tissue.

Solution to Problem

To achieve the above object, the present inventors conducted intensive investigations and found that when a gel-forming polymer material being capable of forming a gel at a temperature of −5° C. or higher and having a main chain resistant to in vivo enzymatic cleavage is used, gelation may be carried out, without using any crosslinking agent, under desired (i.e., less harmful to living cells or living tissue to be embedded) pH and temperature conditions, enabling gelation under optimum conditions for living cells or living tissue. In a verification experiment using a PVA resin having a certain syndiotacticity (preferably a PVA resin having a syndiotacticity of 32 to 40% in triad) as a most preferable embodiment, it was confirmed that it is possible to obtain a PVA-gel cell (or tissue) preparation having a high survival rate of cells or tissue in the PVA gel and a high capability of supplying a physiologically active substance. The present inventors conducted further examination and completed the present invention.

That is, the present invention relates to the following (1) to (23).

(1) A cell or tissue embedding device having an aqueous gel serving as an immunoisolation layer, the aqueous gel containing, as a component thereof, a polyvinyl alcohol resin having a syndiotacticity of 32 to 40% in triad (A).

(2) The cell or tissue embedding device according to the above (1), wherein the aqueous gel has a history of gelation at a temperature of −5° C. or higher.

(3) The cell or tissue embedding device according to the above (1) or (2), wherein the aqueous gel has a stress of 0.3 to 30 kPa.

(4) The cell or tissue embedding device according to any one of the above (1) to (3), wherein the polyvinyl alcohol resin (A) has a saponification degree of 90 to 99.99 mol % and a polymerization degree of 100 to 10000.

(5) The cell or tissue embedding device according to any one of the above (1) to (4), wherein the polyvinyl alcohol resin (A) is a saponification product of a polymer having vinyl pivalate as a polymerizable component thereof and comprises a vinyl pivalate unit.

(6) The cell or tissue embedding device according to any one of the above (1) to (5), wherein a biological component (B) and a cell culture component (C) are embedded in the immunoisolation layer.

(7) The cell or tissue embedding device according to the above (6), wherein the biological component (B) is one or more selected from the group consisting of pancreatic islet cells, pancreatic ductal cells, liver cells, nerve cells, thyroid cells, parathyroid cells, kidney cells, adrenal cells, pituitary cells, splenic cells, fat cells, bone marrow cells, mesenchymal stem cells, ES cells, and iPS cells.

(8) The cell or tissue embedding device according to the above (6), wherein the biological component (B) is pancreatic islet cells or liver cells.

(9) The cell or tissue embedding device according to any one of the above (6) to (8), wherein the cell culture component (C) is an acetate or phosphate buffer containing one or more selected from the group consisting of Na, K, Cl, Ca, and glucose.

(10) The cell or tissue embedding device according to any one of the above (1) to (9), comprising a supporting base (D).

(11) The cell or tissue embedding device according to the above (10), wherein the material of the supporting base (D) is one or more selected from the group consisting of PET, PE, PP, polytetrafluoroethylene sold under the trademark TEFLON, and metal.

(12) The cell or tissue embedding device according to any one of the above (1) to (11), having a stress of 0.3 to 30 kPa.

(13) A method for producing the cell or tissue embedding device according to any one of the above (6) to (12), comprising the steps of mixing an aqueous solution containing a polyvinyl alcohol resin (A), with a cell culture component (C), subsequently mixing a biological component (B) therewith, and subjecting the obtained mixture to gelation.

(14) The method for producing the cell or tissue embedding device according to the above (13), wherein an aqueous gel is prepared at a temperature of −5° C. or higher.

(15) An immunoisolation layer forming agent for a cell or tissue embedding device, the agent containing an aqueous gel containing a polyvinyl alcohol resin having a syndiotacticity of 32 to 40% in triad (A).

(16) The agent according to the above (15), wherein the polyvinyl alcohol resin (A) has a saponification degree of 90 to 99.99 mol % and a polymerization degree of 100 to 10000.

(17) The agent according to the above (16), wherein the polyvinyl alcohol resin (A) is a saponification product of a polymer having vinyl pivalate as a polymerizable component thereof and comprises a vinyl pivalate unit.

(18) A cell or living tissue embedding device having an aqueous gel serving as an immunoisolation layer, the aqueous gel containing a polyvinyl alcohol resin (A) and allowing penetration of a component secreted by a biological component (B) embedded therein while inhibiting penetration of immune-related cells or an immune-related substance. (Here, the component secreted by the biological component (B) is preferably a physiologically active substance, such as a hormone and a protein, useful for a living organism).

(19) Use of the aqueous gel according to any one of the above (1) to (12) and (15) to (17), for producing the device according to any one of the above (1) to (12).

(20) A method for preventing or treating a disease in a human or an animal, characterized in that the device according to any one of the above (1) to (12) is administered to a human or an animal.

(21) The device according to any one of the above (1) to (12) for use in preventing or treating a disease in a human or an animal.

(22) A mixture containing a polyvinyl alcohol resin having a syndiotacticity of 32 to 40% in triad (A), a biological component (B), and a cell culture component (C), the mixture having a property of forming a gel at a temperature of −5° C. or higher.

(23) A method for forming a protecting gel layer for cells or tissue producing a physiologically active substance, the method comprising applying, to the cells or tissue, an aqueous solution or a sol of a protecting gel layer-forming material containing a gel-forming polymer material having a main chain resistant to in vivo enzymatic cleavage, the cells or tissue being optionally supported on a supporting material, and then subjecting the solution or sol to gelation at a temperature of −5° C. or higher.

Advantageous Effects of Invention

Since the cell or tissue embedding device of the present invention is produced using a gel-forming polymer material having a main chain resistant to in vivo enzymatic cleavage, a long device life can be achieved when applied into a living organism. In addition, since the cell or tissue embedding device of the present invention is produced without any crosslinking agent component and an aqueous gel can be formed at a pH and a temperature (preferably –5° C. or higher) less harmful to the living cells or living tissue to be embedded or less likely to kill the living cells or living tissue to be embedded, the device is highly capable of supplying a physiologically active substance, such as a hormone or a protein, useful for a patient. The gel-forming polymer material having a main chain resistant to in vivo enzymatic cleavage may be crosslinked by a crosslinking agent component as desired.

That is, the cell or tissue embedding device of the present invention achieves long-term durability and achieves a high survival rate of the cells or tissue embedded therein.

In addition, by administering the cell or tissue embedding device of the present invention to a patient, prevention and/or treatment of a disease, such as an endocrine disease, a metabolic disease, diabetes, a neurodegenerative disease, hemophilia, a bone disease, and cancer, can be performed and the cells or tissue can be stably held in a living organism for a long period of time. Therefore, a high cure rate can be achieved and the frequency of the cell or tissue embedding device transplantation can be reduced.

Furthermore, the aqueous gel, such as the aqueous PVA gel as a representative embodiment of the present invention (herein, may be referred to as an aqueous gel of the present invention), can inhibit penetration of complements in addition to leucocytes, antibodies, etc., and therefore, can isolate the environment from not only cells and antibodies participating in immunity but also complements that assist immunological effects. That is, the aqueous PVA gel of the present invention allows penetration of molecules having a diameter of about 5 nm, which presumably corresponds to the diameter of the maximum one among various molecules that should be passed therethrough, including oxygen, inorganic and organic nutrients, and various hormones (for example, physiologically active substances including hormones, such as insulin) while the aqueous PVA gel does not allow penetration of molecules having a diameter of about 50 nm, which presumably corresponds to the diameter of the minimum one among immune-related cells and immune-related substances (for example, antibodies and complements) that should not be passed therethrough. Due to the selectivity, the aqueous PVA gel can be used as an immunoisolation layer, having an excellent immunosuppressive effect.

DESCRIPTION OF EMBODIMENTS

Figure 1:
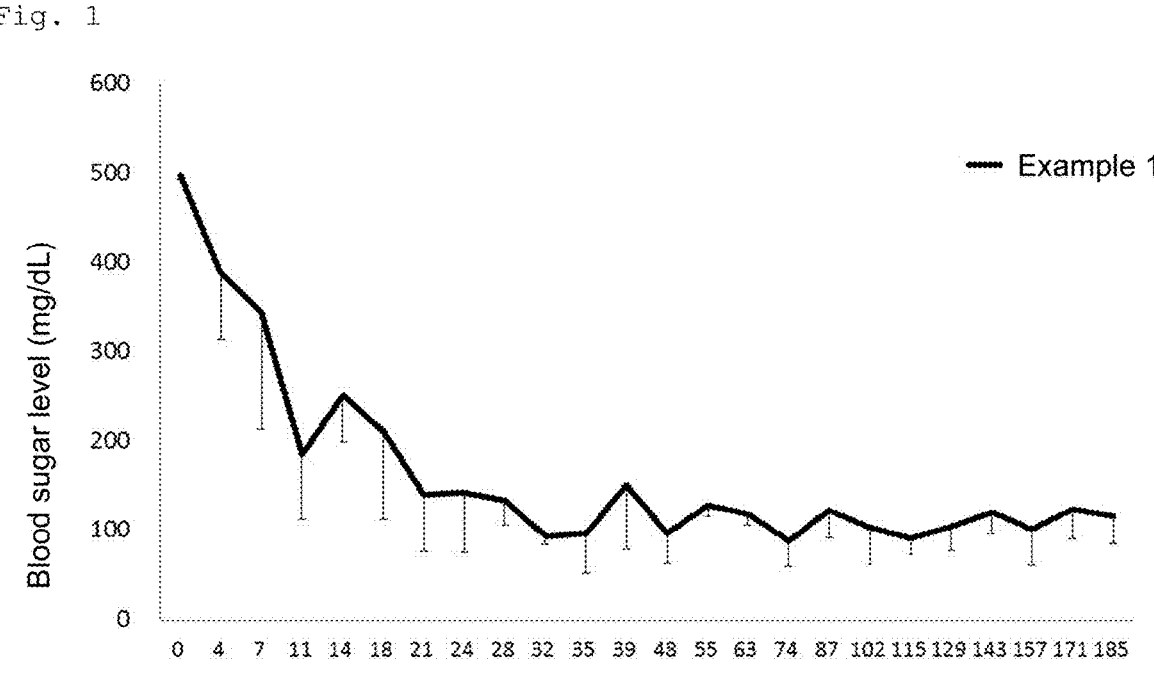
FIG. 1 shows the temporal change of the blood sugar levels of diabetic model animals after transplantation of the bioartificial pancreatic islet device of Example 1.

Hereinafter, the present invention will be described in detail.

The disclosure encompasses a cell or tissue embedding device having an aqueous gel serving as an immunoisolation layer, the aqueous gel containing, as a component thereof, a gel-forming polymer material having a main chain resistant to in vivo enzymatic cleavage. The gel-forming polymer material can be prepared in the form of an aqueous solution or an aqueous sol, is capable of forming a gel at a temperature of –5° C. or higher, and is exemplified by a polyvinyl alcohol resin having a syndiotacticity of 32 to 40% in triad (A).

A representative embodiment of the aqueous gel of the present invention is an aqueous gel for forming an immunoisolation layer of a cell or tissue embedding device, the aqueous gel containing, as a component thereof, a PVA resin having a controlled syndiotacticity (in more detail, a PVA resin having a syndiotacticity of 32 to 40% in triad). The PVA resin in a gel state is prepared by subjecting an aqueous solution or a sol containing the PVA resin to temperature reduction to not lower than –5° C.

In this disclosure, the sol is preferably a hydrosol.

A Gel-Forming Polymer Material Having a Main Chain Resistant to In Vivo Enzymatic Cleavage The gel-forming polymer material used in the present invention having a main chain resistant to in vivo enzymatic cleavage, unlike gelatin or alginic acid as an aqueous gel-forming material used for the same purpose, is preferably a polymer material having a main chain resistant to in vivo enzymatic cleavage, and, for example, may additionally have a main chain to be broken at either or both ends as long as the principal part is not broken. Such a material is exemplified by a polymer having an ethylene structure as a main chain of its repeating unit, in particular, a polyvinyl alcohol resin and a polyacrylic acid resin, and among them, preferred is one having, in its side chain, a functional group which is hydrophilic and contributes to gel formation. When such a material is used, even if the device is left in a living organism for a long time, the main chain is resistant to in vivo enzymatic cleavage, and therefore, the form of the device can be retained for a long time.

The gel-forming polymer material having a main chain resistant to in vivo enzymatic cleavage used in the present invention is preferably one which, after prepared in the state of an aqueous solution or an aqueous sol, can be treated in such a state at a temperature at the time of application to living cells, i.e., a temperature between 0° C. and 60° C., and then made into a gel by being left stand at a temperature not lower than –5° C. As well known, temperature-dependent formation of an aqueous gel occurs as a result of crosslinking due to physical interaction between functional groups of side chains of a polymer material. A representative example of the physical interaction is hydrogen bonding between polar groups having active hydrogen, in particular, hydrogen bonding between hydroxyl groups, and other examples include hydrophobic interaction due to hydrophobic groups contained in a hydrophilic polymer, etc.

The gel-forming temperature can be controlled by, for example, adjusting the proportion of functional groups in the entire resin or facilitating structural interaction in the resins. In the case of a PVA resin, in addition to the method of inserting, to a side chain, a special functional group contributing to the interaction, a method of controlling the tacticity of the main chain of the resin may also be employed to facilitate the interaction between hydroxyl groups in the resin, and thereby achieves gel formation at a relatively high temperature.

Hereinafter, detailed description will be given based on a case where a polyvinyl alcohol resin having a syndiotacticity of 32 to 40% in triad is used as a representative embodiment of the present invention.

PVA Resin (A)

The syndiotacticity in triad of the PVA resin (A), which is used in the present invention as a representative example of the gel-forming polymer material having a main chain resistant to in vivo enzymatic cleavage, is usually 32 to 40%, preferably 33 to 39%, and more preferably 34 to 38%. When the syndiotacticity is 32% or higher, the resin easily turns into a gel, and when the syndiotacticity is 40% or less, an aqueous gel can easily be prepared.

The syndiotacticity in triad can be determined from the peak for the hydroxyl group which appears in proton NMR measurement using the PVA resin (A) dissolved in deuterated-DMSO.

The production method of the PVA resin (A) used in the present invention is not particularly limited as long as the syndiotacticity is 32 to 40% in triad, and the PVA resin (A) can easily be obtained by the method in which a vinyl ester polymer obtained by a conventionally known method is saponified. That is, the PVA resin used in the present invention is a saponification product of a vinyl ester polymer.

The method for producing the vinyl ester polymer is not particularly limited as long as it is a method for polymerizing vinyl ester monomers, and any conventionally known method may be employed.

In the polymerization, the shape of the polymerization vessel, the type of the polymerization agitator, the polymerization temperature, the pressure in the polymerization vessel, etc. may be the same as those in a publicly known method. For the polymerization, various conventionally known methods, such as bulk polymerization, solution polymerization, suspension polymerization, emulsion polymerization, etc. may be employed. Considering the control of the polymerization degree and saponification performed after the polymerization, solution polymerization using an alcohol as a solvent or suspension polymerization using water or a combination of water and an alcohol as a dispersion medium is preferred, but the method is not limited to these.

Examples of the vinyl ester monomer include vinyl esters, such as fatty acid vinyl esters and non-fatty acid vinyl esters (for example, vinyl formate, aromatic carboxylic acid vinyl esters, etc.), and from the viewpoints including obtaining a PVA having a high syndiotacticity, preferred are $C_{3-15}$ fatty acid vinyl esters (for examples, linear or branched $C_{3-15}$ fatty acid vinyl esters, such as vinyl propionate, vinyl butyrate, and vinyl pivalate, preferably $C_{3-10}$ fatty acid vinyl esters, such as linear or branched $C_{3-10}$ fatty acid vinyl esters, etc.), $C_{3-15}$ fatty acid vinyl esters having one or more substituents (for example, a halogen group), such as vinyl trifluoroacetate and vinyl trichloroacetate, vinyl formate, etc. These vinyl esters may be used alone or in combination of two or more kinds thereof.

Examples of the method for producing the PVA resin (A) include, in particular, a method in which a vinyl ester having a bulky side chain, such as vinyl propionate, vinyl butyrate, and vinyl pivalate, is homopolymerized or copolymerized, and then saponified using an alkaline catalyst, and a method in which a vinyl ester having a high polarity, such as vinyl formate, vinyl trifluoroacetate, and vinyl trichloroacetate, is homopolymerized or copolymerized, and then saponified using an alkaline catalyst. Among them, a method in which vinyl pivalate is polymerized and then saponified using an alkaline catalyst is preferably used. In Examples below, a production example giving a PVA resin having a syndiotacticity of 37.1% in triad is described. Reduction of the syndiotacticity to less than 37.1% in triad can be achieved by, for example, allowing vinyl acetate to coexist in the polymerization of vinyl pivalate and thereby obtaining a copolymer of vinyl pivalate and vinyl acetate or by raising the polymerization temperature. Increase of the syndiotacticity to more than 37.1% in triad can be achieved by, for example, lowering the polymerization temperature in the above production example. In any case, the syndiotacticity in triad of the obtained PVA resin (A) can be determined from the peak for the hydroxyl group which appears in proton NMR measurement using the PVA resin (A) dissolved in deuterated-DMSO, and therefore, a PVA resin having a syndiotacticity in the range of 32 to 40% can be appropriately selected and used for the present invention.

In the vinyl ester polymer, in addition to the above-mentioned vinyl esters, other unsaturated monomers capable of copolymerizing with vinyl esters may be contained as long as the effects of the present invention are not impaired.

Examples of such other unsaturated monomers may be one or more kinds selected from carboxyl group-containing unsaturated monomers, such as (meth)acrylic acid, maleic acid, maleic anhydride, fumaric acid, crotonic acid, itaconic acid, and undecylenic acid; unsaturated dibasic-acid mono-alkyl esters, such as monomethyl maleate and monomethyl itaconate; amide group-containing unsaturated monomers, such as acrylamide, dimethylacrylamide, dimethylamino-ethylacrylamide, diethylacrylamide, dimethylaminopropy-lacrylamide, isopropylacrylamide, N-methylolacrylamide, and N-vinylacetamide; vinyl halides, such as vinyl chloride and vinyl fluoride; glycidyl group-containing unsaturated monomers, such as allyl glycidyl ether and glycidyl meth-acrylate; lactam group-containing unsaturated monomers, such as N-vinyl-pyrrolidones, such as N-vinyl-2-pyrroli-done and N-vinyl-alkyl-pyrrolidone, such as N-vinyl-mono- or di-Ci-4 alkyl-pyrrolidone, such as N-vinyl-3-propyl-2-pyrrolidone, N-vinyl-5-methyl-2-pyrrolidone, N-vinyl-5-ethyl-2-pyrrolidone, N-vinyl-5,5-dimethyl-2-pyrrolidone, and N-vinyl-3,5-dimethyl-2-pyrrolidone; N-allyl-pyrrolido-nes, such as N-allyl-2-pyrrolidone; N-vinyl-piperidones, such as N-vinyl-2-piperidone and N-vinyl-alkyl-piperidone, such as N-vinyl-mono- or di-$C_{1-4}$ alkyl-piperidones, such as N-vinyl-6-methyl-2-piperidone and N-vinyl-6-ethyl-2-pip-eridone; N-vinyl-caprolactams, such as N-vinyl-epsilon-caprolactam and N-vinyl-alkyl-caprolactam, such as N-vi-nyl-mono- or di-$C_{1-4}$ alkyl-caprolactams, such as N-vinyl-7-methyl-2-caprolactam and N-vinyl-7-ethyl-2-caprolactam; alkyl vinyl ethers, such as $C_{1-20}$ alkyl vinyl ethers, such as methyl vinyl ether, n-propyl vinyl ether, i-propyl vinyl ether, n-butyl vinyl ether, i-butyl vinyl ether, t-butyl vinyl ether, lauryl vinyl ether, dodecyl vinyl ether, and stearyl vinyl ether; nitriles, such as acrylonitrile and methacrylonitrile; hydroxyl group-containing unsaturated monomers, such as $C_{1-20}$ monoalkyl allyl alcohols, such as allyl alcohol and isopropenyl allyl alcohol, $C_{1-20}$ dialkyl allyl alcohols, such as dimethyl allyl alcohol, and hydroxy $C_{1-20}$ alkyl vinyl ethers, such as hydroxy ethyl vinyl ether and hydroxybutyl vinyl ether; acetyl group-containing unsaturated monomers, such as $C_{1-20}$ alkyl allyl acetates, such as allyl acetate, dimethylallyl acetate, and isopropenylallyl acetate; (meth)acrylic acid esters, such as (meth)acrylic acid alkyl esters, such as (meth)acrylic acid $C_{1-20}$ alkyl esters, such as methyl (meth)acrylate, ethyl (meth)acrylate, 2-ethylhexyl acrylate, and n-butyl acrylate; vinylsilanes, such as trimethoxyvinylsilane, tributylvinylsilane, and diphenylmethylvinyl silane; polyoxyalkylene (meth)acrylates, such as polyoxyethylene (meth)acrylate and polyoxypropylene (meth)acrylate; polyoxyalkylene (meth)acrylamides, such as polyoxyethylene (meth)acrylamide and polyoxypropylene (meth)acrylamide; polyoxyalkylene vinyl ethers, such as polyoxyethylene vinyl ether and polyoxypropylene vinyl ether; polyoxyalkylene alkylvinyl ethers, such as polyoxyethylene allyl ether, polyoxypropylene allyl ether, polyoxyethylene butylvinyl ether, and polyoxypropylene butylvinyl ether; α-olefins, such as ethylene, propylene, n-butene, and 1-hexene; butenes, such as 3,4-dihydroxy-1-butene, 3,4-diacyloxy-1-butene, 3-acyloxy-4-hydroxy-1-butene, 4-acyloxy-3-hydroxy-1-butene, and 3,4-diacyloxy-2-methyl-1-butene; pentenes, such as 4,5-dihydroxy-1-pentene, 4,5-diacyloxy-1-pentene, 4,5-dihydroxy-3-methyl-1-pentene, and 4,5-diacyloxy-3-methyl-1-pentene; hexenes, such as 5,6-dihydroxy-1-hexene and 5,6-diacyloxy-1-hexene; amine unsaturated monomers, such as N,N-dimethylallylamine, N-allylpiperazine, 3-piperidine acrylic acid ethyl ester, 2-vinylpyridine, 4-vinylpyridine, 2-methyl-6-vinylpyridine, 5-ethyl-2-vinylpyridine, 5-butenylpyridine, 4-pentenylpyridine, and 2-(4-pyridyl)allyl alcohol; quaternary ammonium compound-containing unsaturated monomers, such as dimethylaminoethyl acrylate methyl chloride quaternary salt, N,N-dimethylaminopropylacrylamide methyl chloride quaternary salt, and N,N-dimethylaminopropylacrylamide methyl benzenesulfonate quaternary salt; aromatic unsaturated monomers, such as styrene; sulfonic acid group-containing unsaturated monomers, such as 2-acrylamide-2-methylpropanesulfonic acid or its alkali metal salt, ammonium salt or organic amine salt, 2-acrylamide-1-methylpropanesulfonic acid or its alkali metal salt, ammonium salt or organic amine salt, 2-methacrylamide-2-methylpropanesulfonic acid or its alkali metal salt, ammonium salt or organic amine salt, vinyl sulfonic acid or its alkali metal salt, ammonium salt or organic amine salt, allyl sulfonic acid or its alkali metal salt, ammonium salt or organic amine salt, and methallyl sulfonic acid or its alkali metal salt, ammonium salt or organic amine salt; glycerol monoallyl ether; 2,3-diacetoxy-1-allyloxypropane; 2-acetoxy-1-allyloxy-3-hydroxypropane; 3-acetoxy-1-allyloxy-3-hydroxypropane; 3-acetoxy-1-allyloxy-2-hydroxypropane; glycerol monovinyl ether; glycerol monoisopropenyl ether; acryloyl morpholine; vinyl ethylene carbonate; vinylimidazole; and vinylcarbazole.

The amount of such other unsaturated monomers is not particularly limited, and for example, may be 10 mol or less relative to 100 mol of the vinyl ester monomer.

In the polymerization, a polymerization catalyst may be used. The polymerization catalyst is not particularly limited, and an azo compound or a peroxide is usually used.

During the polymerization, an organic acid, such as tartaric acid, citric acid, and acetic acid, may be added for the purpose of preventing the hydrolysis of the aliphatic vinyl ester.

To terminate the polymerization, a polymerization terminator may be optionally used. The polymerization terminator is not particularly limited, and examples thereof include m-dinitrobenzene etc.

The polymerization temperature is not particularly limited and may be a known polymerization temperature. However, from the viewpoints including obtaining a PVA resin having a high syndiotacticity, the temperature is, for example, −5 to 200° C., preferably −5 to 150° C., and more preferably 0 to 120° C.

A vinyl ester polymer is obtained in the manner described above. The method for saponifying the obtained polymer is not particularly limited, and a conventionally known method may be employed. For example, a conventionally known alcoholysis or hydrolysis using a basic catalyst, such as sodium hydroxide, potassium hydroxide, and sodium methoxide, or an acidic catalyst, such as hydrochloric acid, sulfuric acid, and p-toluenesulfonic acid, is applicable. Usually, the syndiotacticity of a polymer hardly changes before and after saponification.

Examples of the solvent used for the saponification include alcohols, such as methanol and ethanol; esters, such as methyl acetate and ethyl acetate; ketones, such as acetone and methyl ethyl ketone; aromatic hydrocarbons, such as benzene and toluene; tetrahydrofuran, etc., and these may be used alone or in combination of two or more kinds. The saponification temperature, saponification time, etc. are not particularly limited.

Also, the method for drying, grinding, or washing the saponification product is not particularly limited, and a publicly known method may be used.

Thus, a saponification product of a vinyl ester polymer, i.e., the PVA resin (A) of the present invention is obtained. As long as the effects of the present invention are not hindered, the obtained PVA resin (A) may be post-denatured by a known method using a reaction, such as acetalization, urethanation, etherification, grafting, phosphorylation, acetoacetylation, cationization, etc.

The saponification degree of the PVA resin (A) is preferably 90 to 99.99 mol %, more preferably 98 to 99.99 mol % (for example, 98.0 to 99.97 mol %), and still more preferably 99 to 99.99 mol % (for example, 99 to 99.95 mol %). The saponification degree of a PVA resin can be determined by $^1$H-NMR measurement in a deuterated-DMSO solution.

The polymerization degree of the PVA resin (A) is preferably 100 to 10000, more preferably 500 to 8000, and still more preferably 1000 to 5000. For relatively easy handling, 1000 to 3000 is particularly preferred. For example, the polymerization degree of the PVA resin is within the range of, 1000 to 2000, 2000 to 3000, 3000 to 4000, or 4000 to 5000. When the polymerization degree is 100 or higher, an aqueous gel having high resin strength (stress) and shape retainability can easily be prepared. When the polymerization degree is 10000 or lower, an aqueous solution of the resin can easily be handled. The polymerization degree is that of the resin before saponification and is a value converted to the polymerization degree of polyvinyl acetate in a benzene solution at 30° C. determined as described in JIS K-6725.

The crosslinking rate, the void ratio, and/or the average pore diameter of the aqueous PVA gel of the present invention may be adjusted such that the selectivity of the aqueous PVA gel is not impaired. The selectivity of the aqueous PVA gel means that the aqueous PVA gel allows penetration of molecules having a diameter of about 5 nm, which presumably corresponds to the diameter of the maximum one among various molecules that should be passed therethrough, including oxygen, inorganic and organic nutrients, and various hormones (for example, physiologically active substances including hormones, such as insulin) while the aqueous PVA gel does not allow penetration of molecules having a diameter of about 50 nm, which presumably corresponds to the diameter of the minimum one among immune-related cells and immune-related substances (for example, antibodies and complements) that should not be passed therethrough. Examples of a method useful for such adjustment include the complement penetration blocking test.

The average pore size of the aqueous PVA gel of the present invention is, for example, 5 nm or more and less than 500 nm, preferably 5 nm or more and less than 200 nm, and more preferably 5 nm or more and less than 50 nm.

The average pore size can be determined by, for example, by photographing (SEM image, 1000× to 5000× magnification) the gel surface using a scanning electron microscope (Hitachi S-4000 made by Hitachi, Ltd.), importing the obtained image into an image processor (main body: TV image processor TVIP-4100II made by Nippon Avionics Co., Ltd; control software: TV image processor image command 4198 made by Ratoc System Engineering Co., Ltd.) to measure the sizes of a predetermined number of pores, and then arithmetically processing the sizes.

Alternatively, the average pore size can be determined using an atmospheric force scanning electron microscope (for example, AeroSurf 1500, made by Hitachi High-Technologies; and JASM-6200 made by JEOL, Ltd.), or by dynamic light scattering (for example, nano Partica SZ-100-Plus made by Horiba, Ltd.), scanning microscopic light scattering, etc.

Biological Component (B)

By embedding a biological component (B) in the aqueous gel of the present invention, a cell or tissue embedding device can be formed.

The biological component (B) is not particularly limited, and can be appropriately selected according to the intended use of the cell or tissue embedding device to be produced.

The biological component (B) is preferably cells (preferably living cells) or living tissue that can be stably stored at a temperature preferable for the production of the aqueous gel of the present invention (i.e., −5 to 60° C.) because, in this case, a cell or tissue embedding device highly capable of supplying a physiologically active substance can be obtained regardless of the kind of the cells or living tissue.

As such cells, differentiated cells, stem cells, or the like derived from ectoderm, mesoderm, or entoderm can be used, for example.

As the differentiated cells, for example, epidermal cells, smooth muscle cells, bone cells, bone marrow cells, cartilage cells, skeletal myoblasts, pancreatic parenchymal cells, pancreatic islet cells, pancreatic endocrine cells, pancreatic exocrine cells, pancreatic ductal cells, liver cells (for example, hepatocytes), thyroid cells, parathyroid cells, adrenal cells, pituitary cells, splenic cells, pineal cells, renal cells (nephrocytes), spleen cells, anterior pituitary cells, somatotropic cells, dopamine-producing cells, blood cells, cardiac muscle cells, skeletal muscle cells, osteoblast cells, nerve cells, pigment cells, fat cells, etc. can be used. The above cells are not limited to cells isolated from a living organism and may be cells differentiated from stem cells described later.

As for stem cells (iPS cells etc.) and other cells that can be induced to differentiate, the cells may be embedded in the device, and after administration, differentiated in a living organism. Alternatively, the cells may be differentiated beforehand and then embedded in the device.

The stem cells may be tissue stem cells (for example, epidermal stem cells, hair follicle stem cells, pancreatic stem cells/pancreatic progenitor cells, liver stem cells, neural stem cells, retinal stem cells, hematopoietic stem cells, mesenchymal stem cells, etc.), embryonic stem cells (ES cells), iPS cells (induced pluripotent stem cells), etc., but are not limited thereto.

These cells are preferably from a mammal, such as a human, a swine, a rat, or a mouse, and preferably produce and/or secrete a physiologically active substance, such as a hormone or a protein, useful for a living organism, such as a patient. The kind of the cells to be selected may be determined depending on the kind of the disease in the living organism, such as a patient, to undergo the transplantation. In the cases where these cells are not human cells, they may be cells having a human gene introduced thereinto for therapeutic purposes. The hormone useful for a living organism may be exemplified by insulin, thyrotropic hormone, thyroid hormone, parathyroid hormone, growth hormone, thyroxine, glucocorticoid, glucagon, estradiol, and testosterone. The protein useful for a living organism may be exemplified by, in particular, a blood coagulation factor, a complement, albumin, globulin, and various enzymes (metabolic enzymes or digestive enzymes, such as amylase, protease, and lipase). Examples of other physiologically active substances include neurotransmitters, such as dopamine.

Specifically, the cells are preferably pancreatic cells (pancreatic islet cells), hepatocytes, dopamine-producing cells, and stem cells and progenitor cells thereof, more preferably pancreatic cells (pancreatic islet cells), hepatocytes, and stem cells and progenitor cells thereof, and more preferably pancreatic cells (pancreatic islet cells) and pancreatic progenitor (stem) cells.

The biological component (B) used in the present invention may be cells or living tissue established for laboratory use, cells separated from living tissue, or the like, and preferably differentiated non-dividing cells. The separation method is not particularly limited, and the separation may be performed according to a conventionally known method. Desirably, cells separated from living tissue are subjected to removal of pathogens, such as pathogenic viruses.

In the cell or tissue embedding device of the present invention, the amount of the biological component (B) may be appropriately changed according to the kind of the biological component (B) and is not particularly limited. The content is, for example, 1000 to 1000000 cells, preferably 10000 to 100000 cells, and more preferably 20000 to 50000 cells per cubic millimeter of the gel device embedding space.

The dosage amount cannot be definitely specified because it is determined on a case-by-case basis by a doctor in consideration of the patient's age, sex, and conditions, side effects, etc., but usually, the number of devices to be transplanted in the body per adult is about 1 to 10. For example, into a diabetic patient, usually 1000 to 100000 IEQ (international unit of the number of pancreatic islets: 1 IEQ corresponds to the volume of one islet with a diameter of 150 μm), preferably 5000 to 40000 IEQ, more preferably 10000 to 20000 IEQ per kg of the patient's body weight contained in one or more devices may be transplanted.

The shape of the device is not particularly limited. The shape may be discoidal, globular, cylindrical, ellipsoidal, or the like, and a discoidal shape is preferred. When the device is discoidal, the size may be represented as the product of the thickness and the diameter. The thickness is usually 0.1 mm to 10 cm, preferably 0.1 to 5 mm, and more preferably 0.5 to 2 mm, and the diameter is usually about 1 mm to 50 cm, preferably about 1 mm to 10 cm, and more preferably about 2 to 4 cm.

A conventionally known material may be used in the device.

As the biological component (B) in the present invention, in addition to the above-described cells or living tissue, other components of biological origin may be included.

The disclosure encompasses cases other than the cases where cells or tissue in the cell or tissue embedding device of the present invention is from living microorganisms.

Cell Culture Component (C)

In the aqueous gel of the present invention, a cell culture component (C) may be embedded together with the biological component (B) to form a cell or tissue embedding device.

The cell culture component (C) is not particularly limited, and examples thereof include an acetate or phosphate buffer containing Na, K, Cl, Ca, and glucose.

When Na is contained in the cell culture component (C), the Na concentration is preferably adjusted to 20 to 150 mEq/L, and more preferably adjusted to 80 to 140 mEq/L.

When K is contained, the K concentration is preferably adjusted to 2.5 to 130 mEq/L, and more preferably adjusted to 3.5 to 40 mEq/L.

When Cl is contained, the Cl concentration is preferably adjusted to 15 to 170 mEq/L, and more preferably adjusted to 100 to 150 mEq/L.

When Ca is contained, the Ca concentration is preferably adjusted to 0.5 to 5 mEq/L, and more preferably adjusted to 1 to 3 mEq/L.

When glucose is contained, the glucose concentration is preferably adjusted to 1 to 11 mM, and more preferably adjusted to 3 to 7 mM.

The cell culture component (C) is not particularly limited, and examples thereof include a publicly known cell culture medium, such as HBSS (Hanks' balanced salt solution), a commercial preservation solution, such as Euro-Collins solution, CELLBANKER, and UW solution (University of Wisconsin solution), a cellular protection component, such as dimethyl sulfoxide (DMSO) and serum albumin, a component for preventing contamination by germs, such as an antibiotic, a component for retaining cell activity, such as vitamins, such as nicotinamide, etc., and a publicly known cell culture medium or the like is preferred. These may be used alone or in combination of two or more kinds thereof.

The cell culture component (C) may be used in combination with another component (for example, a sustained-releasability imparting agent, a tonicity agent, a pH adjuster, etc.).

Since the PVA resin (A) and the cell culture component (C) are in contact with each other in the device of the present invention, when the cell culture component (C) is added in the preparation of the device, it is convenient to add the cell culture component (C) at a concentration as high as "(the volume of the solution containing polyvinyl alcohol resin (A)+the volume of cell culture component (C))/the volume of cell culture component (C)" times the final concentration.

The amount of the cell culture component (C) in this state is not particularly limited, but the content is preferably such that the growth, survival, and/or physiologically active substance secretion of the cells or the living tissue is not inhibited and the object of the present invention is not impaired.

The amount of the cell culture component (C) added in the state described above may be, for example, about 100 to 2000 parts by mass, preferably about 150 to 1000 parts by mass (for example, 200 to 300 parts by mass, 175 to 300 parts by mass, etc.) relative to 100 parts by mass of the PVA resin (A).

For example, the cell culture component (C) at a concentration as high as 10 times the final concentration may be 1 mL relative to 9 mL of the PVA resin (A) solution.

In the preparation of the cell or tissue embedding device, components other than the PVA resin (A), the biological component (B), and the cell culture component (C) may be used.

Examples of such other components include a cell growth factor, which is a substance that promotes or controls the growth of living cells, a cytokine, which is an active substance produced from a cell, another physiologically active substance, a blood-flow promoter, which promotes the blood flow to the cell or tissue embedding device, a neurotrophic factor, etc. These may be used alone or in combination of two or more kinds thereof.

Examples of the cell growth factor include a platelet derived growth factor (PDGF), an epidermal growth factor (EGF), a fibroblast growth factor (FGF), a hepatocyte growth factor (HGF), a vascular endothelial growth factor (VEGF), insulin, etc.

Examples of the cytokine include a hematopoietic factor (for example, interleukins, chemokines, a colony-stimulating factor, etc.), a tumor necrosis factor, interferons, etc.

Examples of the physiologically active substance other than the cell growth factor and the cytokine include amino acids (for example, glycine, phenylalanine, lysine, aspartic acid, glutamic acid, etc.), vitamins (for example, biotin, pantothenic acid, vitamin D, etc.), serum albumin, an antibiotic, etc.

Examples of the blood-flow promoter include citrulline or its salt, capsaicin, and capsaicinoids.

Examples of the neurotrophic factor include NGF (nerve growth factor), BDNF (brain-derived neurotrophic factor; brain-derived neurotrophic factor), NT-3 (neurotrophin-3), NT-4 (neurotrophin-4), GDNF (glial-cell derived neurotrophic factor), neurturin, artemin, persephin, etc.

The amounts of the above components are not particularly limited.

Aqueous Gel

The aqueous gel used in the cell or tissue embedding device of the present invention can be prepared without particular limitation, as long as it is an aqueous gel prepared by dissolving a PVA resin (A) in an aqueous solvent and then subjecting the solution to gelation. The method for dissolving the PVA resin (A) is not particularly limited, and for example, heating, stirring, or the like may be performed for the dissolution. The dissolution may be performed in a sealed state, and may be performed under pressurization as needed. As the aqueous solvent, water is usually used.

The aqueous gel of the present invention can be obtained by, for example, dissolving the PVA resin (A) in an aqueous solvent with heating at 90° C. or higher, followed by cooling.

The conditions for preparing the solution are not particularly limited as long as the conditions allow the PVA resin (A) to dissolve in water, and the heating temperature is, for example, 90 to 250° C., preferably 105 to 230° C., and more preferably 110 to 200° C. When the heating temperature is 100° C. or higher, the PVA resin easily dissolves. When the heating temperature is 250° C. or lower, the PVA resin is less likely to be decomposed.

The time for the dissolution may be appropriately changed depending on the temperature, pressure, solution concentration, etc., and is, for example, 1 minute to 12 hours, 30 minutes to 10 hours, etc.

In the preparation of the aqueous gel of the present invention, any apparatus may be used for the dissolution in water. Specific examples of the apparatus include autoclaves of rotary type or with stirrer, capable of heating; extruders in the cases where the amount of water is small; etc.

The biological component (B) may be mixed with the aqueous gel after the preparation of the aqueous gel, or alternatively, also added to and mixed with the aqueous solution of the PVA resin (A).

Regarding the cell culture component (C), it is possible that the aqueous gel prepared beforehand is immersed in a solution containing the cell culture component (C), and for curbing the reduction of the number of living cells, the cell culture component (C) may be mixed with the PVA resin (A) (and also the biological component (B) as needed) before the gelation.

The method for preparing the aqueous gel is exemplified by an embodiment where an aqueous solution of the PVA resin (A) is mixed with the cell culture component (C), the biological component (B) is added thereto, and the resulting mixture (may be in a sol state) is subjected to gelation.

The above-mentioned other components that may be used in the present invention may be added together with or separately from the biological component (B) and/or the cell culture component (C), to the PVA resin (A), an aqueous solution of the PVA resin (A), and/or the aqueous gel, and then be mixed therewith.

The aqueous solution of the PVA resin (A) is desirably sterilized by a conventionally known method, such as autoclave treatment, UV or gamma-ray treatment, or the like, and in the mixing with the biological component (B) or subsequent production of the cell or tissue embedding device, the operation and storage are desirably performed under a germ-free environment.

The pH of the mixture of the PVA resin (A) (and also the biological component (B) and/or the cell culture component (C) is mixed therewith as needed) is preferably adjusted to 6.0 to 8.0, more preferably 6.2 to 7.7, and still more preferably 6.5 to 7.5 using a buffer, such as HEPES (2-[4-(2-hydroxyethyl)-1-piperazinyl]ethanesulfonic acid). This range is preferable because living cells or living tissue to be embedded in the cell or tissue embedding device is less likely to be damaged and the reduction of the number of living cells is curbed.

In the preparation of the aqueous gel, the aqueous solution of the PVA resin (A) (and also the biological component (B) and/or the cell culture component (C) mixed therewith as needed) may be left stand.

The temperature at which the mixture is left stand is not particularly limited as long as the temperature is suitable for storing living cells, and is, for example, −5° C. or higher, preferably −5 to 60° C. (for example, 0 to 60° C.), more preferably −3 to 50° C. (for example, 0 to 50° C.), and still more preferably 0 to 40° C. In this range, the reduction of the number of living cells is curbed, which is preferable. The temperature at which the mixture is left stand is preferably such that the aqueous solution (may be in a sol state) or an aqueous gel of the PVA resin (A) does not freeze and living cells or living tissue can be embedded in the solution or the aqueous gel. In the present invention, by using the PVA resin (A) having a certain syndiotacticity, it is possible to prepare an aqueous gel at a relatively low temperature suitable for storing living cells or living tissue (for example, a temperature within the above range).

The left-stand time for the preparation of the aqueous gel may be appropriately selected depending on the concentration of the PVA resin (A), the left-stand temperature, or the like, and is usually about 1 hour to 3 or 4 days, preferably about 1 hour to 2 days, and more preferably about 2 to 12 hours. One hour or more of the left-stand time is preferred from the viewpoints including that the resulting cell or tissue embedding device does not easily collapse when placed in a living organism.

When the proportion of the number of living cells in the aqueous gel or in the cell or tissue embedding device relative to the total number of the living cells in the biological component (B) immediately before embedded in the aqueous gel is higher as compared to that in the aqueous gel or in the cell or tissue embedding device not containing, as a component thereof, the PVA resin (A) used in the present invention, the cell or tissue embedding device of the present invention can be regarded as achieving a high survival rate of the cells or tissue embedded therein.

The proportion of the number of living cells in the aqueous gel or in the cell or tissue embedding device relative to the total number of the living cells in the biological component (B) immediately before embedded in the aqueous gel is, for example, 60 to 100%, preferably 70 to 100%, and more preferably 80 to 100%. The number of living cells can be determined by, for example, cytoplasmic staining with fluorescein diacetate, and nuclear staining with propidium iodide (sometimes abbreviated to FDA/PI measurement).

The solid concentration in the aqueous gel is, for example, 0.3 to 20%, preferably 0.5 to 10%, and more preferably 1 to 8% (for example, 3 to 8%). When the solid concentration is in the range, after the cell or tissue embedding device is transplanted into an animal, the form and the immunoisolation capability of the device can be retained in the body for a long period of time. In view of such points, the above range is preferable. Herein, the method for measuring the solid concentration is not particularly limited, and may be, for example, a method using a heating-and-drying moisture analyzer (A&D, MS-70) or the like as in Examples described later.

The resulting aqueous gel has a structure suitable for functioning as an immunoisolation layer described later, i.e., a structure that stably maintains cells, allows oxygen, glucose, hormones useful for a living organism such as insulin, and other physiologically active substances to pass therethrough and does not allow immune-related proteins to pass therethrough.

The aqueous gel usually has such a strength (stress) as to prevent easy collapse at the time of transplantation. The stress varies depending on the polymerization degree and the tacticity of the PVA resin (A), and the solid concentration of the aqueous gel, and therefore cannot be simply determined, but for example, the stress is 0.3 to 30 kPa, preferably 0.4 to 25 kPa, more preferably 0.5 to 20 kPa, and still more preferably 0.5 to 15 kPa.

The stress of the aqueous PVA gel can be measured using a compact table-top tester EZ Test EZ-SX made by Shimadzu Corporation, according to the directions for use.

The shape of the aqueous gel is not particularly limited, and examples thereof include sheets, boards, discs, rods, tubes, beads, etc.

Examples of the method for forming the shape of the aqueous gel include a method in which an aqueous solution (may be in a sol state) containing the PVA resin (A) (and also preferably the biological component (B) and the cell culture component (C) as desired) is poured into a mold having an intended shape before gelation, a method in which an obtained gel is shaped into an intended shape with a knife or the like, etc.

Usually, the aqueous solution containing the PVA resin (A) (and also the biological component (B) and/or the cell culture component (C) etc. as desired) goes through a sol state before reaching the gel state. Such a sol state shall be regarded as an equivalent to the aqueous gel of the present invention and is understood to be also included in the present invention.

The solid concentration in the aqueous solution (may be in a sol state) containing the PVA resin (A) is, for example 0.3 to 20%, preferably 0.5 to 10%, and more preferably 1 to 8%. When the solid concentration is in the range, after the cell or tissue embedding device is transplanted into an animal, the form and the immunoisolation capability of the device can be retained in the body for a long period of time. In view of such points, the above range is preferable.

Cell or Tissue Embedding Device

The aqueous gel of the present invention can be used as an immunoisolation layer of a cell or tissue embedding device.

The "immunoisolation layer" means a layer that allows penetration of, for example, glucose; hormones, such as insulin, thyrotropic hormone, thyroid hormone, parathyroid hormone, growth hormone, thyroxine, glucocorticoid, glucagon, estradiol, and testosterone; proteins, such as a blood coagulation factor, albumin, globulin, and various enzymes (metabolic enzymes or digestive enzymes, such as amylase, protease, and lipase); neurotransmitters, such as dopamine; etc., but does not allow penetration of, for example, immune-related proteins, such as antibodies, complements, and leucocytes.

The cell or tissue embedding device embeds or contains the biological component (B), and may be, for example, a bio-artificial organ.

The method for producing the cell or tissue embedding device is not particularly limited, and for example, by storing (for example, for about 1 hour to 3 or 4 days, about 2 to 48 hours, or about 3 to 24 hours) an aqueous solution or an aqueous gel containing the PVA resin (A) containing the biological component (B) and the cell culture component (C) in a mold having an intended shape at a temperature of 0 to 40° C. (for example, 4° C.), a cell or tissue embedding device can be produced.

The cell or tissue embedding device usually has such a strength (stress) as to prevent easy collapse at the time of transplantation. The stress varies depending on the polymerization degree and the tacticity of the PVA resin (A), the added amount of the cell culture component (C), and the solid concentration of the cell or tissue embedding device, and therefore cannot be simply determined, but for example, the stress is 0.3 to 30 kPa, preferably 0.4 to 25 kPa, more preferably 0.5 to 20 kPa, and still more preferably 0.5 to 15 kPa.

The stress of the cell or tissue embedding device can be measured using a compact table-top tester EZ Test EZ-SX made by Shimadzu Corporation, according to the directions for use.

The cell or tissue embedding device of the present invention may comprise a supporting base (D).

The aqueous gel may be used in combination with a supporting base (D) useful as a reinforcing material for the reinforcement and/or easier handling.

For example, in cases where the aqueous gel is formed into a thin film, gelation is preferably performed on a base (reinforcing material) such as a resin mesh sheet for the reinforcement and easier handling.

The material of the supporting base (D) is not particularly limited, and examples thereof include polymers (for example, PET (polyethylene terephthalate), PE (polyethylene), PP (polypropylene), polytetrafluoroethylene sold under the trademark TEFLON, etc.), metals, and the like. The material is preferably not altered or decomposed in a living organism, but may be decomposed after a certain period of time.

The mesh size of the mesh sheet is determined such that the mesh allows penetration of molecules having a diameter of about 5 nm, which presumably corresponds to the diameter of the maximum one among various molecules that should be passed therethrough, including oxygen, inorganic and organic nutrients, and various hormones (for example, physiologically active substances including hormones, such as insulin) while the mesh does not allow penetration of molecules having a diameter of about 50 nm, which presumably corresponds to the diameter of the minimum one among immune-related cells and immune-related substances (for example, antibodies and complements) that should not be passed therethrough. For this reason, the mesh size is usually 5 to 100 nm, preferably 10 to 50 nm, and more preferably 20 to 30 nm.

A preferred embodiment of the cell or tissue embedding device of the present invention has, for example, a configuration obtained as follows. On a glass slide, an aqueous solution or an aqueous gel containing a PVA resin (A) containing the cell culture component (C) is placed; on this, a supporting base (D), such as a PET mesh (for example, trade name: PET mesh sheet TN120 etc. made by SAN-PLATEC Corp.) is placed; on the PET mesh sheet, a suspension obtained by suspending a biological component (B) in an aqueous solution or an aqueous gel containing a PVA resin (A) is placed; the suspension is spread over the PET mesh using a gel loading tip etc.; a PET mesh is further placed thereon in such a manner that the suspension is between the PET meshes; further on the PET mesh, an aqueous solution or an aqueous gel containing a PVA resin (A) containing the cell culture component (C) is placed; on this, a glass slide is placed; and the glass slides are removed. Before the glass slides are removed, the cell or tissue embedding device is preferably left stand at a temperature of 0 to 40° C. (for example, 4° C.) for 2 to 48 hours, and more preferably for 3 to 24 hours.

The cell or tissue embedding device of the present invention can be transplanted by being placed in a body, such as under the skin, under the fascia, on the liver surface, on the spleen surface, in the greater omentum, or in the abdominal cavity of an animal including a human. The method for placing the device is not particularly limited, and a conventionally known method may be employed. For example, an instrument used for the transplantation may be a publicly known one.

By transplanting the cell or tissue embedding device of the present invention into an animal including a human having an endocrine disease (for example, a thyroid disease, a parathyroid disease, an adrenal disease, a pituitary disease, a pineal disease, etc.), a metabolic disease (for example, ornithine transcarbamylase deficiency, hyperammonemia, hypercholesterolemia, homocystinuria, glycogenosis, Crigler Najjar syndrome, Wilson's disease, etc.), diabetes (for example, Type 1 diabetes, Type 2 diabetes, pancreatic diabetes, etc.), a neurodegenerative disease (for example, Parkinson's disease, Alzheimer disease, amyotrophic lateral sclerosis, spinocerebellar degeneration, etc.), hemophilia, a bone disease (for example, osteoporosis etc.), cancer (for example, leukemia etc.), etc., the prevention and/or the therapy of the diseases can be achieved. Since the cell or tissue embedding device of the present invention can retain the cells in a stable state in a living organism, these diseases can be treated at a high cure rate, and the frequency of the cell or tissue embedding device transplantation can be reduced.

Furthermore, the aqueous gel of the present invention can inhibit penetration of, in addition to particles having a particle diameter of 5 to 50 μm (for example, leucocytes (for example, macrophages etc.), lymphocyte (for example, T lymphocyte etc.), etc.), particles having a particle diameter of 0.1 to 1 μm (for example, complements etc.). Therefore, the cell or tissue embedding device of the present invention can isolate the environment from immune-related cells and complements, and for this reason, can be used as an excellent immunoisolation layer.

As a preferable embodiment, a case where the cells are pancreatic islet cells, for example, will be described.

Figures 3, 4:
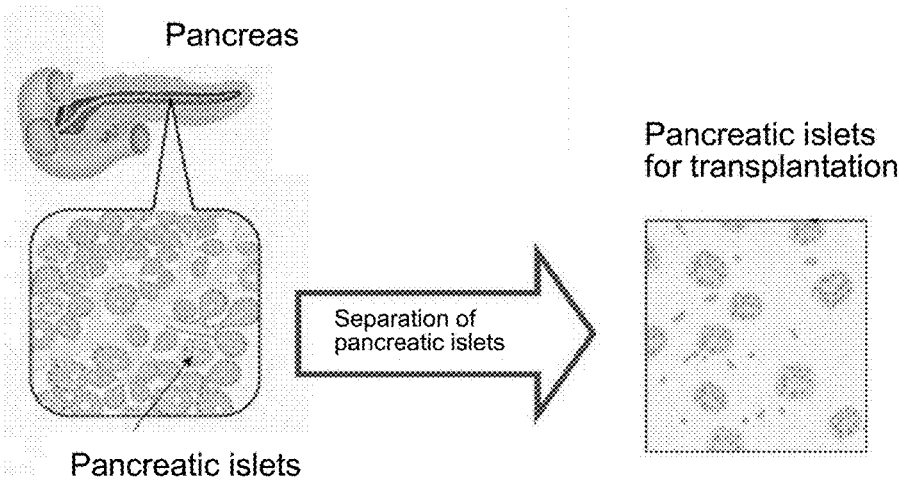
FIG. 3 shows the temporal change of the blood sugar levels of diabetic model animals after transplantation of the frozen and thawed pancreatic islet devices of Comparative Examples 6 to 11.
FIG. 4 schematically shows an embodiment of a method for obtaining pancreatic islet cells from the pancreas.
Figure 5:
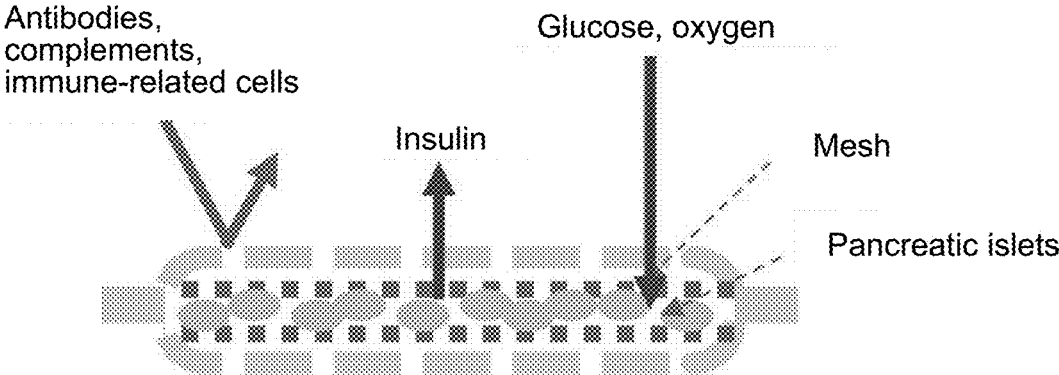
FIG. 5 shows one embodiment of a cell or tissue embedding device having an aqueous gel serving as an immunoisolation layer, the aqueous gel containing, as a component thereof, a polyvinyl alcohol resin (A).

As shown in FIG. 4, pancreatic islet cells of good quality are separated from the pancreas to prepare pancreatic islets for transplantation (see FIG. 4). In order to prevent aggregation of the pancreatic islet cells, the cells are fixed between the above-described meshes (two sheets). From the thus-prepared pancreatic islet cells in the fixed state and the PVA resin (A), the device of the present invention is produced, where the most inner layer is pancreatic islet cells secreting insulin. The second layer is a mesh layer supporting the cells. The outermost layer is a gel surface forming an immunoisolation membrane. The immunoisolation membrane has a high biocompatibility, and allows insulin to pass therethrough but does not allow immune-related substances to pass therethrough (see FIG. 5).

Figure 6:
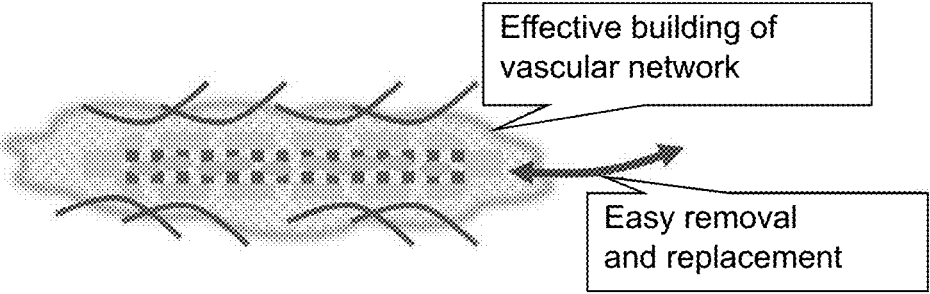
FIG. 6 schematically shows an example of a state where the device of the present invention is administered into and accommodated in a network of neovascular vessels.

The device of the present invention can be applied as it is into a living organism, and is, for example, accommodated in a network built of neovascular vessels, which can be easily provided according to the known art, to exhibit a medical effect. The device can be easily taken out or replaced (see FIG. 6).

This device can provide at least one of the following features.

(1) Maintains high quality of the cells embedded.

(2) Appropriately isolates the transplanted pancreatic islets from the host patient's immune system.

(3) Receives supply of oxygen and glucose and provides appropriate insulin response.

(4) Enables less invasive transplantation and can be easily taken out of the body or replaced as needed.

The cell or tissue embedding device of the present invention preferably does not have a semipermeable membrane.

EXAMPLES

Hereinafter, the present invention will be illustrated in more detail by Examples, but the present invention is not limited thereto. Various modifications can be made within the technical idea of the present invention by those with ordinary skill in the art. In Examples, "parts" and "%" express "parts by mass" and "% by mass" unless otherwise stated.

Physical properties of PVA resin (A)

(1) Syndiotacticity

The syndiotacticity in triad (%) was determined by $^1$H-NMR measurement in a $d_6$-DMSO solution.

The syndiotacticity in triad (%) is determined from the ratio of three hydroxyl protons in the range of 4 to 5 ppm (from the lower magnetic field side, isotactic [I], heterotactic [H], and syndiotactic [S]) and based on the following formula.

$$\text{Syndiotacticity in triad } (\%) = [S]/([I]+[H]+[S]) \times 100$$

(2) Saponification Degree

The saponification degree (mol %) was determined by $^1$H-NMR measurement in a $d_6$-DMSO solution.

(3) Polymerization Degree

The polymerization degree converted to the polymerization degree of polyvinyl acetate in a benzene solution at 30° C. was determined as described in JIS K-6725.

Preparation of PVA Resin (A)

Synthetic Example 1

Into a flask equipped with a stirrer, a thermometer, a dropping funnel, and a reflux condenser, 800 parts of vinyl pivalate and 190 parts of methanol were placed. After nitrogen replacement of the system, the jacket was heated to 80° C. At the time when reflux occurred, a solution of 0.07 part of 2,2'-azobis(2,4-dimethylvaleronitrile) dissolved in 10 parts of methanol was added to start polymerization. At 6 hours from the start, m-dinitrobenzene as a polymerization terminator was added to stop the polymerization. The polymerization yield was 58%.

After removing methanol and vinyl pivalate from the obtained reaction mixture, acetone was added to dissolve poly vinyl pivalate, giving a 40% acetone solution.

To 250 parts of this 40% acetone solution, 110 parts of a 25% methanol solution of potassium hydroxide was added and thoroughly mixed therewith, and saponification was allowed to proceed at 50° C. for 2 hours. The obtained gelatinous material was pulverized, and saponification was further allowed to proceed in 150 parts of acetone and 340 parts of a 25% methanol solution of potassium hydroxide at 50° C. for 4 hours. After the reaction, the mixture was neutralized with acetic acid, solid liquid separation was performed, and the solid was washed with methanol and water and then dried to give 30 g of PVA resin 1.

The obtained PVA resin 1 had a polymerization degree before saponification of 1450 and a saponification degree of 99.91 mol %. The syndiotacticity in triad was 37.1%.

Synthetic Example 2

The same procedure was performed as in Synthetic Example 1 except that 800 parts of vinyl pivalate was changed to 685 parts of vinyl pivalate and that 115 parts of vinyl acetate was added, to prepare PVA resin 2. The molar ratio of vinyl pivalate/vinyl acetate was 80/20. The obtained PVA resin 2 had a polymerization degree before saponification of 1510 and a saponification degree of 99.90 mol %. The syndiotacticity in triad was 35.7%.

Synthetic Example 3

The same procedure was performed as in Synthetic Example 1 except that 800 parts of vinyl pivalate was changed to 553 parts of vinyl pivalate and that 247 parts of vinyl acetate was added, to prepare PVA resin 3. The molar ratio of vinyl pivalate/vinyl acetate was 60/40. The obtained PVA resin 3 had a polymerization degree before saponification of 2030 and a saponification degree of 99.89 mol %. The syndiotacticity in triad was 34.0%.

Synthetic Example 4

Into a flask equipped with a stirrer, a thermometer, a dropping funnel, and a reflux condenser, 2000 parts of vinyl pivalate and 38 parts of methanol were placed. After nitrogen replacement of the system, the jacket was heated to 80° C. At the time when reflux occurred, a solution of 0.03 part of 2,2'-azobis(2,4-dimethylvaleronitrile) dissolved in 2 parts of methanol was added to start polymerization. At 3 hours from the start, m-dinitrobenzene as a polymerization terminator was added to stop the polymerization. The polymerization yield was 17%.

After removing methanol and vinyl pivalate from the obtained reaction mixture, acetone was added to dissolve poly vinyl pivalate, giving a 25% acetone solution.

To 200 parts of this 25% acetone solution, 54 parts of a 25% methanol solution of potassium hydroxide was added and thoroughly mixed therewith, and saponification was allowed to proceed at 50° C. for 2 hours. The obtained gelatinous material was pulverized, and saponification was further allowed to proceed in 150 parts of acetone and 168 parts of a 25% methanol solution of potassium hydroxide at 50° C. for 4 hours. After the reaction, the mixture was neutralized with acetic acid, solid liquid separation was performed, and the solid was washed with methanol and water and then dried to give 17 g of PVA resin 4.

The obtained PVA resin 1 had a polymerization degree before saponification of 4440 and a saponification degree of 99.86 mol %. The syndiotacticity in triad was 36.7%.

Synthetic Example 5

The same procedure was performed as in Synthetic Example 4 except that 2000 parts of vinyl pivalate was changed to 1600 parts of vinyl pivalate and that 268 parts of vinyl acetate was added, to prepare PVA resin 5. The molar ratio of vinyl pivalate/vinyl acetate was 80/20. The obtained PVA resin 1 had a polymerization degree before saponification of 4530 and a saponification degree of 99.93 mol %. The syndiotacticity in triad was 35.5%.

Preparation of Aqueous Solution A (Aqueous Solution of PVA Resin (A) in a Sol State As the aqueous solution A, which is an aqueous solution of PVA resin (A) in a sol state, 2 kinds of aqueous solutions of PVA resin (A) in a sol state containing the cell culture medium (C) were prepared. The prepared sol-state aqueous solutions of PVA resin (A) may be hereafter written as sol A-1 and sol A-2.

Sol A-1

With 23.575 g of distilled water, 1.425 g of the above PVA resin 1 was mixed, dissolved with stirring at 35 rpm at 160° C. for 3 hours to prevent burning or the like, and cooled to 90° C. The resulting sol-state aqueous solution of PVA resin (A) was collected into a glass vial warmed to 90° C. beforehand, and kept at 90° C. Then, the prepared sol-state aqueous solution of PVA resin (A) was placed in a water bath at 42° C. To 8.8 mL of the sol-state aqueous solution of PVA resin (A), 1.0 mL of HBSS (Hanks' balanced salt solution) at 10-fold concentration and 0.2 mL of 1 M HEPES were added, and the tube was shaken up and down for agitation. Then, spinning down was performed using a centrifuge (trade name: Hybrid high-speed refrigerated centrifuge 6200 made by Kubota Corporation), and the tube was left stand at 42° C. to give sol A-1 (PVA resin concentration: 5 w/v %). The obtained sol A-1 was transferred to a 3.5-cm dish.

Sol A-2

With 23.865 g of distilled water, 1.135 g of the above PVA resin 1 was mixed, dissolved with stirring at 35 rpm at 160° C. for 3 hours to prevent burning or the like, and cooled to 90° C. The resulting sol-state aqueous solution of PVA resin (A) was collected into a glass vial warmed to 90° C. beforehand, and kept at 90° C. Then, the prepared sol-state aqueous solution of PVA resin (A) was placed in a water bath at 42° C. To 8.8 mL of the sol-state aqueous solution of PVA resin (A), 1.0 mL of HBSS (Hanks' balanced salt solution) at 10-fold concentration and 0.2 mL of 1 M HEPES were added, and the tube was shaken up and down for agitation. Then, spinning down was performed using a centrifuge (trade name: Hybrid high-speed refrigerated centrifuge 6200 made by Kubota Corporation), and the tube was left stand at 42° C. to give sol A-2. The obtained sol A-2 was transferred to a 3.5-cm dish.

Solid Concentration Measurement of Sols A-1 and A-2

The solid concentrations of the sols A-1 and A-2 prepared above was measured in the following manner.

The solid concentration of the sol was measured using a heating-and-drying moisture analyzer (A&D, MS-70). On the sample dish of the moisture analyzer, a glass fiber sheet was placed, and about 1 g of the sol was allowed to uniformly permeate into the sheet. Then, the solid content of the sol was measured under the conditions of the sample dish temperature of 120° C. and the measuring time (warming time) of 15 minutes. In the measurement, the moisture analyzer was set in a mode for displaying the solid content (%). The formula for calculating the solid content is mass after drying/mass before drying×100(%). The calculated solid concentration of the sol A-1 was 6.5% by mass, and the calculated solid concentration of the sol A-2 was 5.5% by mass.

Preparation of Pancreatic Islet Cells

For separation of pancreatic islets, 11 to 14-week-old male Lewis rats (Japan SLC, Inc.) were used. A cold Hanks' balanced salt solution (HBSS) containing 0.8 mg/mL of collagenase type V (made by Sigma-Aldrich) dissolved therein was injected, through the rat common bile duct, to the pancreas of the rat, and the pancreas was digested at 37° C. for 12 minutes to separate pancreatic islets from the pancreatic tissue. Concentration gradient centrifuge was performed using Histopaque-1119 (made by Sigma-Aldrich) and Lymphoprep (AXIS-SHIELD, Norway), and pancreatic islets were collected. The pancreatic islets were cultured in a RPMI 1640 culture medium containing 5.5 mmol/L of glucose and 10% fetal bovine serum (FBS) under 5% $CO_2$ at 37° C. overnight, and were used in the examination of Examples and the Comparative Examples.

Preparation of Pancreatic Islet Embedding Devices

On a glass slide, 60 μL of the above-prepared sol A-1 or A-2 on the dish was placed, and left stand at 4° C. for 10 minutes. A circular PET mesh having a diameter of 15 mm (trade name: PET mesh sheet TN120 made by SANPLATEC Corp.) was placed thereon, and a suspension obtained by suspending the above-prepared pancreatic islet cells from which the culture medium components had been removed as thoroughly as possible in 60 μL of the sol A-1 or A-2 was placed on the PET mesh. The suspension of the pancreatic islet cells was spread over the PET mesh using a gel loading tip, and a PET mesh was further placed thereon in such a manner that the suspension of the pancreatic islet cells was between the PET meshes. Further on the PET mesh, 250 μL of the sol A-1 or A-2 was placed, and on this, a glass slide was placed. The thus-built sol was placed in a moist chamber, and left stand at 4° C. for 3 hours to give a pancreatic islet embedding device (aqueous gel). The number of pancreatic islets of both of the above pancreatic islet embedding devices was 800 IEQ.

Step of storing Pancreatic Islet Embedding Device

Example 1

The pancreatic islet embedding device (aqueous gel) using the sol A-1 built as above was taken off the glass slides, soaked in 5 mL/well of a preservation medium (RPMI 1640 culture medium containing glucose adjusted to a concentration of 5.5 mM and 10% FBS) in a 6-well plate, and stored at 4° C. for about 2 hours.

Test Example 1 (Transplantation Test 1)

The sol A-1-based pancreatic islet embedding device (aqueous gel) stored at 4° C. for about 2 hours was transplanted under the skin of a C57BL/6J mouse with streptozotocin-induced diabetes.

Evaluation of Healing of Diabetes

After the above transplantation, time-depending changes in the blood sugar level were measured to examine the healing effect (n=4). The mean±SD is shown in FIG. 1 and Table 1. A blood sugar level of 200 mg/dL or lower was judged as Good (diabetes was healed) and a blood sugar level of higher than 200 mg/dL was judged as Poor (a state of diabetes).

As shown in FIG. 1, the diabetic model animals into each of which the pancreatic islet embedding device of the present invention was transplanted showed reduction in the blood sugar level from immediately after the transplantation, and even at 185 days after the transplantation, the improvement in the blood sugar level was still observed.

Also, harvesting the pancreatic islet embedding device at 180 days after the transplantation under the skin was attempted. In each case of Example 1 (n=4), the device favorably retained its form without any collapse, demonstrating that the cell or tissue embedding device of the present invention was strong enough not to be decomposed in the body.

Also in the case of 6 w/v % of PVA resin (A), reduction in the blood sugar level was observed from immediately after the transplantation, and even at 185 days after the transplantation, the improvement in the blood sugar level was still observed.

Comparative Example 1

Composition of PVA Solution

For the preparation of a pancreatic islet device to be frozen and thawed, a PVA solution containing 3% PVA (having a polymerization degree of 5000, a saponification degree of 99.3 mol %, and a syndiotacticity of 29.5% in triad), 10% FBS (fetal bovine serum), 5% dimethyl sulfoxide, and 10 mM nicotinamide obtained by dissolving the solutes in an ETK (ET-Kyoto) solution was used.

Step of Embedding Pancreatic Islet Cells

In a 1.5-mL tube, Lewis rat pancreatic islet cells from which the culture medium components had been removed as thoroughly as possible were placed. To this, 1.0 mL of a cell banker (Juji Field Inc.) at 4° C. was added, and the pancreatic islet cells were suspended. After the cells were left stand on ice for 1 minute, the cell banker was removed. On a glass slide with a 1-mm spacer, a PET mesh (trade name: PET mesh sheet TN120, 10×15 mm, made by SANPLATEC Corp.) having the above PVA solution applied thereon was placed. Over the PET mesh, a suspension obtained by suspending only pancreatic islet cells in 160 μL of the PVA solution was spread, and on this, a PET mesh having the PVA solution applied thereon was placed. On this, a glass slide was placed, and thus a 1-mm thick pancreatic islet device to be frozen and thawed was prepared.

Step of Freezing, Thawing, and Storage

The prepared pancreatic islet device to be frozen and thawed was left stand at −80° C. for 24 hours, taken off the glass slides, and thawed in an ice-cooled UW solution (University of Wisconsin solution, organ preservation solution). Further, the device was soaked in the ice-cooled UW solution three times (for 5 minutes each) to replace the solution in the gel by the UW solution, and then stored in the UW solution at 4° C. for 24 hours.

Step of Culture

The UW solution on the surface of the device was washed off with 10 mL of an ice-cooled culture medium for pancreatic islet culture (RPMI1640 culture medium containing 5.5 mM glucose, 10% FBS, and an antibiotic). After that, the device was soaked in the culture medium (ice-cooled) three times (for 5 minutes each) to replace the solution in the gel by the culture medium, and then cultured in 3 mL of the culture medium at 37° C. for 24 hours.

Step of Transplantation

Transplantation was performed by placing the frozen and thawed pancreatic islet device after the above storage in the abdominal cavity of a C57BL/6J mouse with streptozotocin-induced diabetes, regarding which mouse graft survival was known to be more successful in the abdominal cavity than under the skin.

Evaluation of Healing of Diabetes

After the transplantation, in the same manner as in Example 1, the blood sugar level was measured over time, and the healing effect was evaluated. The results are shown in Table 1 and FIG. 2.

Comparative Examples 2 to 18

As shown in Table 2, except that the number of pancreatic islets and the number of devices to be transplanted were changed, frozen and thawed pancreatic islet devices were prepared and transplanted, and healing of diabetes was evaluated in the same manner as in Comparative Example 1. The results are shown in Table 1 and FIGS. 2 and 3.

In Table 1, the blood sugar levels at 185 days after transplantation are shown for Example 1, and the blood sugar levels at 28 days after transplantation are shown for Comparative Examples 1 to 18.

TABLE 1

| | Blood sugar level at 185 days or 28 days after transplantation (mg/dL) | Evaluation of healing of diabetes |
|---|---|---|
| Example 1 | 116 | Good |
| Comparative Example 1 | 501 | Poor |
| Comparative Example 2 | 501 | Poor |
| Comparative Example 3 | 461 | Poor |
| Comparative Example 4 | 432 | Poor |
| Comparative Example 5 | 501 | Poor |
| Comparative Example 6 | 475 | Poor |
| Comparative Example 7 | 436 | Poor |
| Comparative Example 8 | 481 | Poor |
| Comparative Example 9 | No data (Died 1 day after transplantation) | Poor |
| Comparative Example 10 | 492 | Poor |
| Comparative Example 11 | 448 | Poor |
| Comparative Example 12 | No data (Died 1 day after transplantation) | Poor |
| Comparative Example 13 | No data (Died 2 days after transplantation) | Poor |
| Comparative Example 14 | No data (Died 1 day after transplantation) | Poor |
| Comparative Example 15 | No data (Died 1 day after transplantation) | Poor |
| Comparative Example 16 | No data (Died 1 day after transplantation) | Poor |
| Comparative Example 17 | No data (Died 1 day after transplantation) | Poor |
| Comparative Example 18 | No data (Died 1 day after transplantation) | Poor |

TABLE 2

| Comparative Example | Number of pancreatic islets (IEQ) | Number of transplanted devices |
|---|---|---|
| 1 | 1,300 | 1 |
| 2 | | |
| 3 | | |
| 4 | 1,500 | 1 |
| 5 | | |

TABLE 2-continued

| Comparative Example | Number of pancreatic islets (IEQ) | Number of transplanted devices |
|---|---|---|
| 6 | 3,000 | 1 |
| 7 | | |
| 8 | 6,000 | 1 |
| 9 | | |
| 10 | | |
| 11 | | |
| 12 | | |
| 13 | 6,000 | 2 |
| 14 | 6,000 | 2 |
| 15 | 6,000 | 1 |
| 16 | | |
| 17 | 12,000 | 2 |
| 18 | | |

Figure 2:
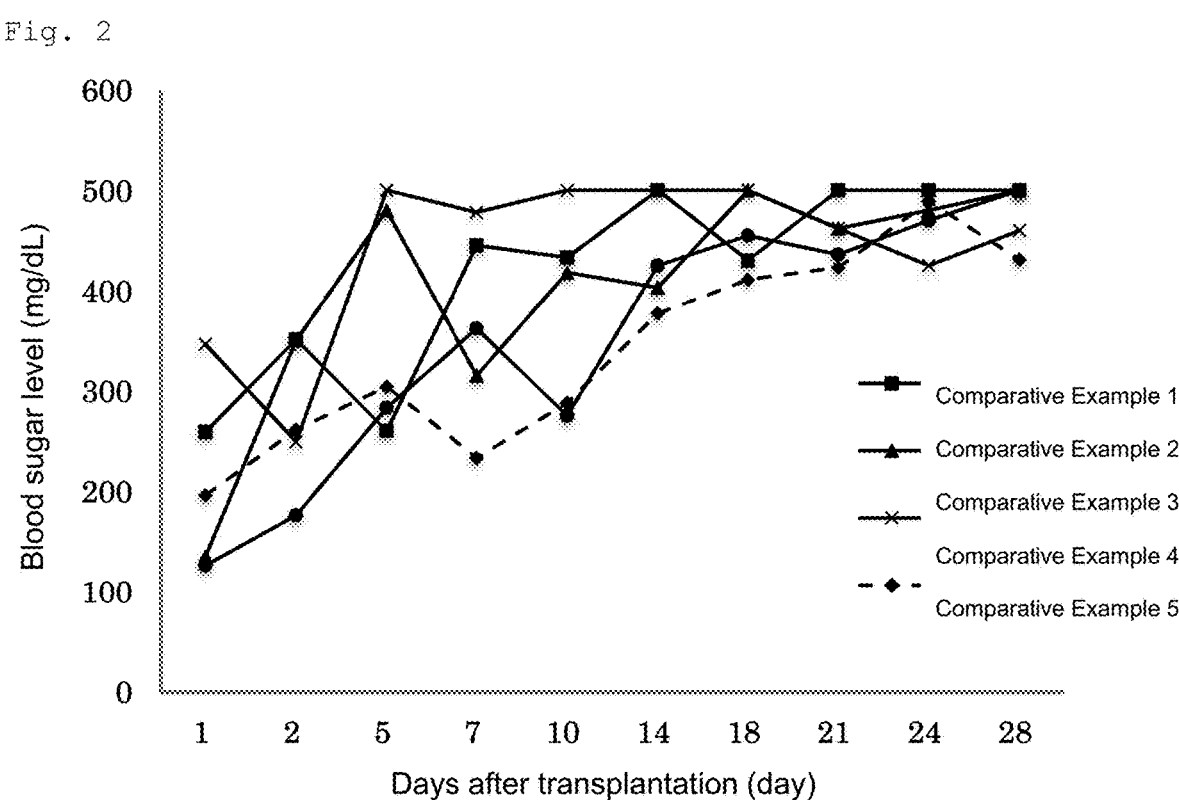
FIG. 2 shows the temporal change of the blood sugar levels of diabetic model animals after transplantation of the frozen and thawed pancreatic islet devices of Comparative Examples 1 to 5.

In the cases of the frozen and thawed bioartificial pancreatic islet devices of Comparative Examples 1 to 18, at the time when the PVA gel was frozen and thawed, the form of the pancreatic islets embedded therein had already collapsed. In an experiment in which the devices were transplanted to diabetic model animals, as shown in FIGS. 2 and 3, although transient decreases in the blood sugar level attributable to graft collapse were observed in some cases, the blood level increased again within 2 weeks after transplantation in all the cases. Thus, the frozen and thawed pancreatic islet devices were proved not to be capable of healing diabetes.

Also, as clearly shown in Table 1, the cell or tissue embedding device of Example 1 of the present invention exhibited a healing effect on diabetes due to the pancreatic islet cells embedded therein while Comparative Examples 1 to 18 did not exhibit any healing effect on diabetes. In Comparative Examples 1 to 18, the pancreatic islet grafts were significantly damaged at the time of transplantation, and therefore, even transplanted into the abdominal cavity known to be the most effective site for the transplantation, did not exhibit any healing effect on diabetes. In contrast, the cell or tissue embedding device of Example 1 of the present invention exhibited a healing effect on diabetes even though the devices were transplanted under the skin known to be the least effective site for the transplantation. These results are noteworthy.

The results of Example 1 show that the immunoisolation capability is retained, and therefore, the activity of the embedded cells is favorably retained. For this reason, it is suggested that even when other cells or living tissue is used as the biological component (B), the effects of retaining the immunoisolation capability and of retaining the activity of embedded cells can be obtained.

Test Example 2 (Transplantation Test 2)

The same procedure as in the production method of the sol A-1 was performed except that PVA resin 2 or 3 was used instead of PVA resin 1 to give a sol, and using the obtained sol, a pancreatic islet embedding device (aqueous gel) was prepared. Using the obtained aqueous gels, the same transplantation test as in Test Example 1 was conducted. Both aqueous gels exhibited substantially the same effects as in the case where PVA resin 1 was used.

Test Example 3 (Transplantation Test 3)

The same procedure as in the production method of the sol A-1 was performed except that a PVA resin having a syndiotacticity of 36.5% or 39.1% prepared at a different polymerization temperature was used instead of PVA resin 1 to give a sol, and using the obtained sol, a pancreatic islet embedding device (aqueous gel) was prepared. Using the obtained aqueous gels, the same transplantation test as in Test Example 1 was conducted. Both aqueous gels exhibited substantially the same effects as in the case where PVA resin 1 was used.

Examples 2 to 5

FDA/PI Measurement

The pancreatic islet device was prepared in the same manner as in Example 1 except that the PVA resin (A) and the concentration thereof were changed as shown in Table 3, and was washed twice with 3 mL/well of PBS (room temperature) for 3 minutes each. To 3 mL of PBS in a 6 well plate, 15 μL of a solution of fluorescein diacetate (FDA: Calbiochmem, San Diego, USA) dissolved in acetone (Wako Pure Chemical Industries, Tokyo, Japan) at 5 mg/mL and 20 μL of a solution of propidium iodide (PI: Sigma-Aldrich, St. Louis, Mo., USA) dissolved in distilled water at 0.5 mg/mL were added to give a FDA/PI staining solution. Into this, the washed pancreatic islet device was transferred and stained in the dark for 5 minutes, and then washed with 3 mL of PBS for 3 minutes. The pancreatic islet device was placed on a cover glass (Matsunami Glass Ind., Ltd., Osaka, Japan), and using a fluorescence microscope (BZ-900: KEY-ENCE, Tokyo, Japan), the localization of FDA (excitation wavelength 470/40 nm, absorption wavelength 525/50) and of PI (excitation wavelength 540/25 nm, absorption wavelength 605/60) in the pancreatic islet was observed.

In the FDA measurement (staining), the presence of living cells were confirmed (FDA (+)), and dead cells were hardly observed for all the Examples. Meanwhile, in the PI measurement, cell nuclei were not stained, revealing that dead cells were hardly present as with the results of FDA staining.

TABLE 3

| Example | PVA resin (A) | Concentration of PVA resin (A) | FDA/PI Measurement |
|---|---|---|---|
| 2 | Synthetic Example 2 | 8 | +/− |
| 3 | Synthetic Example 2 | 6 | +/− |
| 4 | Synthetic Example 3 | 5 | +/− |
| 5 | Synthetic Example 3 | 6 | +/− |

Concentration of PVA resin (A): concentration of PVA resin (A) in the device (w/v %)
FDA/PI measurement evaluation criteria: FDA: (+) living cells exist, (−) cytoplasm destroyed, PI: (+) cell nucleus destroyed, (−) living cells exist

Comparative Example 19

The pancreatic islet device prepared in Comparative Example 1 was subjected to the FDA/PI measurement as in the Examples. In the FDA measurement, no stained image was observed, and in the PI measurement, stained cell nuclei were clearly observed. The results of both the measurements confirmed that the pancreatic islets in the device of the Comparative Example widely became necrotic.

Example 6

Solid Concentration and Stress Measurement for
Aqueous Gel and Cell or Tissue Embedding Device A solution prepared using PVA resin 1 and water at 160° C. was cooled to 90° C. and then filled into a column vessel 34 mm in diameter and left stand at 42° C. for 30 minutes and then at 4° C. for 3 hours to prepare an aqueous gel having a diameter of 34 mm and a height of 17 mm.

The obtained aqueous gel had a solid concentration (concentration of PVA resin 1) of 5.0% and a stress of 0.7 kPa at 20° C.

The solids concentration was measured using a heating-and-drying moisture analyzer (A&D, MS-70). On the sample dish of the moisture analyzer, a glass fiber sheet was placed, and about 1 g of the aqueous gel was allowed to uniformly permeate into the sheet. Then, the solid content of the aqueous gel was measured under the conditions of the sample dish temperature of 120° C. and the measuring time (warming time) of 15 minutes. In the measurement, the moisture analyzer was set in a mode for displaying the solid content (%). The formula for calculating the solid content is mass after drying/mass before drying×100(%).

The stress measurement was performed using a compact table-top tester EZ Test EZ-SX made by Shimadzu Corporation, according to the directions for use. Specifically, the stress of the aqueous gel having a diameter of 34 mm and a height of 17 mm was measured at 20% indentation using a cylinder jig 20 mm in diameter.

Examples 7 to 11

Aqueous gels were prepared as in Example 6 except that the type and the concentration of the PVA resin (A) and the left-stand time at 4° C. were appropriately changed as shown in Table 4, and the solid concentration and the stress were measured.

TABLE 4

| Example | PVA resin (A) | Left-stand time at 4° C. | Solid concentration (%) | Stress (kPa) |
|---|---|---|---|---|
| 6 | 1 | 3 hr | 5.0 | 0.7 |
| 7 | 1 | 90 hr | 5.0 | 1.2 |
| 8 | 4 | 3 hr | 5.0 | 1.2 |
| 9 | 1 | 3 hr | 9.6 | 7.2 |
| 10 | 1 | 70 hr | 9.7 | 11.5 |
| 11 | 5 | 43 hr | 9.9 | 6.4 |

Examples 12 to 14

Cell or tissue embedding devices were prepared as in Example 6 except that HBSS (Hanks' balanced salt solution) was used and that the type and the concentration of the PVA resin (A) and the left-stand time at 4° C. were appropriately changed as shown in Table 5, and the solid concentration and the stress were measured.

TABLE 5

| Example | PVA resin (A) | Concentration of PVA resin (A) | Amount of added HBSS | Left-stand time at 4° C. | Solid concentration (%) | Stress (kPa) |
|---|---|---|---|---|---|---|
| 12 | 1 | 5.0 | 1.0 | 3 hr | 5.8 | 0.8 |
| 13 | 1 | 7.0 | 1.0 | 3 hr | 7.8 | 2.0 |
| 14 | 4 | 10.0 | 1.0 | 45 hr | 10.9 | 8.5 |

Concentration of PVA resin (A): concentration of PVA resin (A) in the device (wt %)
Amount of added HBSS: concentration of Hanks' balanced salt solution in the liquid mixture (wt %)

INDUSTRIAL APPLICABILITY

According to the present invention, an aqueous gel capable of retaining its strong structure in pH and temperature conditions less harmful to embedded living cells or living tissue can easily be formed using less toxic components, and therefore, a cell or tissue embedding device which is highly capable of supplying a physiologically active substance, such as a hormone or a protein, useful for a patient and which isolates contained cells or tissue from the biological defense mechanism can be provided.

The invention claimed is:

1. A cell or tissue embedding device having an aqueous gel serving as an immunoisolation layer, the aqueous gel comprising a polyvinyl alcohol resin having a syndiotacticity of 32 to 40% in triad, wherein pancreatic islets are embedded in the immunoisolation layer, wherein the aqueous gel has a gelation at a temperature of −5° C. or higher, and wherein the polyvinyl alcohol resin has a polymerization degree of 1000 to 5000.

2. The cell or tissue embedding device according to claim 1, wherein the aqueous gel has the gelation at the temperature of 0° C. or higher.

3. The cell or tissue embedding device according to claim 1, wherein the aqueous gel has a stress of 0.3 to 30 kPa.

4. The cell or tissue embedding device according to claim 1, wherein the polyvinyl alcohol resin has a saponification degree of 90 to 99.99 mol%.

5. The cell or tissue embedding device according to claim 1, wherein the polyvinyl alcohol resin is a saponification product of a polymer having vinyl pivalate as a polymerizable component thereof and comprises a vinyl pivalate unit.

6. The cell or tissue embedding device according to claim 1, wherein a cell culture component is embedded in the immunoisolation layer.

7. The cell or tissue embedding device according to claim 6, wherein the cell culture component is an acetate or phosphate buffer containing one or more selected from the group consisting of Na, K, Cl, Ca, and glucose.

8. The cell or tissue embedding device according to claim 1, comprising a supporting base.

9. The cell or tissue embedding device according to claim 8, wherein the material of the supporting base is one or more selected from the group consisting of polyethylene terephthalate, polyethylene, polypropylene, polytetrafluoroethylene, and metal.

10. The cell or tissue embedding device according to claim 1, having a stress of 0.3 to 30 kPa.

11. The cell or tissue embedding device according to claim 1, wherein an average pore size of the aqueous gel is 5 nm or more and less than 500 nm.

12. The cell or tissue embedding device according to claim 1, wherein the aqueous gel is in the form of an aqueous solution or an aqueous sol during preparation.

13. A cell or living tissue embedding device having an aqueous gel serving as an immunoisolation layer, the aqueous gel comprising a polyvinyl alcohol resin having a syndiotacticity of 32 to 40% in triad and pancreatic islets, which allows penetration of a component secreted by the pancreatic islets embedded therein while inhibiting penetration of immune-related cells or an immune-related substance, wherein the aqueous gel has a gelation at a temperature of −5° C. or higher, and wherein the polyvinyl alcohol resin has a polymerization degree of 1000 to 5000.

* * * * *